(12) United States Patent
Berndt

(10) Patent No.: US 7,093,482 B2
(45) Date of Patent: Aug. 22, 2006

(54) SYSTEM AND METHOD FOR DETECTING PARTICLES

(75) Inventor: Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/266,823

(22) Filed: Nov. 4, 2005

(65) Prior Publication Data

US 2006/0053870 A1 Mar. 16, 2006

Related U.S. Application Data

(62) Division of application No. 10/629,209, filed on Jul. 28, 2003, now Pat. No. 6,990,852.

(51) Int. Cl.
*G01N 15/06* (2006.01)
(52) U.S. Cl. ............ 73/61.75; 73/61.71; 73/53.01
(58) Field of Classification Search ............. 73/61.75, 73/61.71, 53.01
See application file for complete search history.

(56) References Cited

U.S. PATENT DOCUMENTS

| 5,041,856 | A | * | 8/1991 | Veronesi et al. | ............ 324/204 |
| 5,486,919 | A | * | 1/1996 | Tsuji et al. | ................. 356/484 |
| 5,698,931 | A | * | 12/1997 | Shibata et al. | ............. 310/338 |
| 5,798,831 | A | * | 8/1998 | Hagiwara | ................ 356/237.2 |
| 5,922,946 | A | * | 7/1999 | Hirota et al. | .............. 73/61.75 |
| 6,826,949 | B1 | * | 12/2004 | Berndt | ....................... 73/64.56 |
| 6,990,852 | B1 | * | 1/2006 | Berndt | ...................... 73/61.75 |
| 2004/0092921 | A1 | * | 5/2004 | Kadziauskas et al. | ......... 606/27 |

\* cited by examiner

*Primary Examiner*—Hezron Williams
*Assistant Examiner*—Rodney Frank

(57) ABSTRACT

An acoustic detector based on rupture event scanning ("REVS") with a detection setup allowing the monitoring of REVS signals near the driving frequency and with optimized impedance matching between the REVS crystal and the front-end of the detection circuitry for use in detecting the presence of particles such as bacteria, viruses, or other particulates in liquid samples with extreme high sensitivity.

26 Claims, 18 Drawing Sheets

SYSTEM AND METHOD FOR DETECTING PARTICLES

FIELD OF THE INVENTION

The present invention relates to the field of the detection and identification of infectious diseases. More specifically, the present invention relates to a method and apparatus for the detection of disease-causing particles such as bacteria, viruses and other particulate entities in liquid samples with extremely high sensitivity.

BACKGROUND OF THE INVENTION

Quartz crystal microbalances ("QCM") have been developed as sensitive chemical and biochemical sensing devices and can be used for the detection of disease-related particles such as viruses and bacteria in liquid samples (see e.g. Thompson, M. et al., Analyst Vol. 116, pp. 881–890, 1991; Rickert, J. et al., Biosensors & Bioelectronics Vol. 12, pp. 567–575, 1997; Uttenthaler, E. et al., Biosensors & Bioelectronics 16, 735–743, 2001). In this technology, a binding partner such as an antibody is attached to the surface of a small resonant quartz crystal with a mechanical resonance frequency typically in the 10 to 30 MHz region. If a disease-related particle binds to the antibody, the resonance frequency of the quartz crystal shows a very small shift, whereby such shift in frequency or a correlated phase shift between the electrical excitation and the mechanical vibration is an indication that an antibody-specific binding partner was present in the liquid sample.

A significant improvement in the detection sensitivity of a QCM biosensor has been achieved by applying the technology of rupture event scanning ("REVS"), (see Dultsev, F. N. et al., Langmuir Vol. 16, 5036–5040, 2000; Cooper, M. A. et al., Nature Biotechnology Vol. 19, 833–837, 2001; WO 01/02857 A1 to Klenerman et al.). In the REVS technology, as in the classic QCM technology, a binding partner such as an antibody is attached to the surface of a small resonant quartz crystal with a mechanical resonance frequency typically in the 10 to 20 MHz region. The liquid sample containing bacteria or viruses is brought into contact with the activated crystal surface so that binding events can take place.

After a 30-minute incubation period, the resonant quartz crystal is operated as close as possible to the fundamental mechanical resonance frequency, whereby the driving power for the quartz crystal is monotonously increased, until suddenly the binding between the binding partners is broken up. According to the inventors of REVS, such breaking or "rupture" event can be detected due to the emission of noisy sound waves with a preferred frequency spectrum around the third harmonic of the fundamental resonance frequency. The quartz crystal acts as a sensitive microphone, and the generated electrical signal is monitored via an electric resonance circuit tuned to a frequency close to the third harmonic of the fundamental resonance frequency of the crystal. The REVS technology has the potential of detecting the breaking-away of only a few binding partners, in other words, the technology offers the potential for extreme sensitive detection.

It is very likely that rupture events may also cause even stronger sound signals at or close to the fundamental resonance frequency of the quartz crystal, but due to the high-level driving signal in this frequency region, the weak REVS signal is obscured and can not be detected in prior art detection devices. As mentioned above, the inventors of REVS have, therefore, designed a detection setup where the REVS signal is coupled from the quartz crystal into a parallel resonance circuit tuned to a frequency close to the third harmonic, and from there into a narrow-band electronic receiver. The detection setup as disclosed in WO 01/02857 A1 is shown schematically in FIG. 1.

In the detection setup shown in FIG. 1, G1 is the driving signal generator working at the crystal's fundamental resonance frequency, F. QC is the vibrating quartz crystal, and G2 is a local oscillator working at a frequency $3F+\Delta F$ with $\Delta F$ being a frequency offset of approximately 80 kHz. Generator G2 tunes the lock-in amplifier to the detection frequency $3F+\Delta F$. The quartz crystal QC is connected with the input of the lock-in amplifier via a parallel resonance circuit, tuned also to the frequency $3F+\Delta F$.

The quartz crystal can, near the third harmonic of its fundamental series resonance frequency, be modeled as a signal source for REVS signals with an internal ohmic impedance of about $50\Omega$. The ohmic impedance of the parallel resonance circuit, on the other hand, may be as high as $500\ k\Omega$. This substantial impedance mismatch between the "source" and the front-end of the detection circuitry results in a non-optimized extraction of signal power from the REVS crystal. FIG. 2 illustrates how the detected power depends on the impedance matching between a $50\text{-}\Omega$ source and the detector input impedance. From this figure it can be seen that a parallel resonance circuit with an effective ohmic component of $500\ k\Omega$ may not be an optimum front-end for a REVS detection setup.

In view of the disadvantages in prior art REVS-based acoustic detectors as described above, there exists still a need for a more optimized detection setup in an acoustic detector based on rupture event scanning.

SUMMARY OF THE INVENTION

It is an objective of the present invention to provide an acoustic detector based on rupture event scanning ("REVS") with a detection setup allowing the monitoring of REVS signals near the driving frequency and with optimized impedance matching between the REVS crystal and the front-end of the detection circuitry.

According to an embodiment of the present invention, the above objective is achieved by a method for detecting the presence of particles in a liquid, comprising the steps of providing a piezo-electric crystal that is able to exhibit resonant mechanical vibrations at certain frequencies, and that has at least one surface that is designed so that said particles in said liquid would bind to said at least one surface; bringing said at least one surface in contact with said liquid comprising said particles; driving said crystal into mechanical vibration with a sinusoidal electrical driving signal at a frequency slightly above the fundamental series resonance frequency of said crystal; connecting said crystal with the first input of a balanced comparator circuitry of low input impedance; providing a sinusoidal amplitude- and phase-adjustable cancellation signal at said frequency to the second input of said balanced comparator circuitry; detecting a sinusoidal output signal at said frequency at the output of said balanced comparator circuitry; adjusting the amplitude and phase of said cancellation signal so that said sinusoidal output signal at the output of said balanced comparator circuitry is cancelled out; increasing the amplitudes of said driving signal and said cancellation signal proportional to each other; detecting transient signals at the output of said balanced circuitry; and deriving the conclusion that particles comprised in said liquid had bound to said surface of said crystal from the detection of said transient signals.

BRIEF DESCRIPTION OF THE DRAWINGS

The invention will be more readily understood with reference to the embodiments thereof illustrated in the attached drawing figures, in which.

In the drawing figures, it will be understood that like numerals refer to like features and structures.

DETAILED DESCRIPTION OF THE PREFERRED EMBODIMENTS

Figure 1:
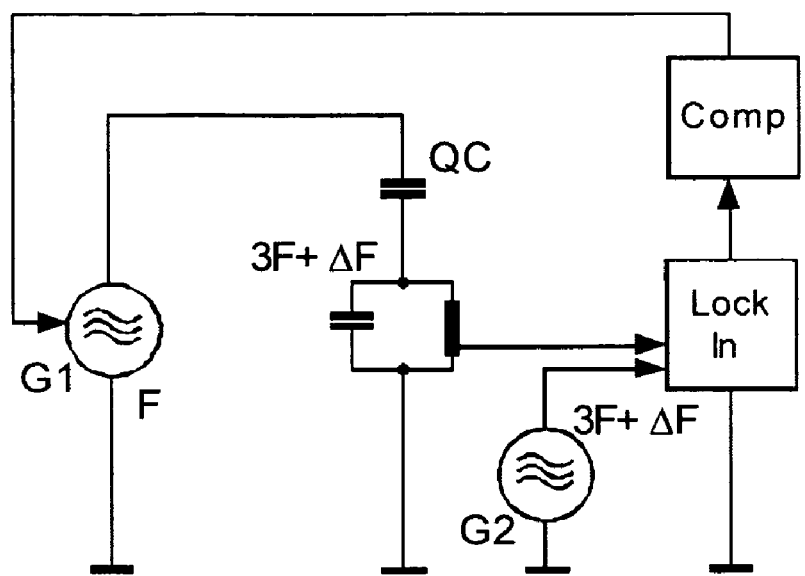
FIG. 1 illustrates a detection setup for rupture event scanning (REVS)
Figure 2:
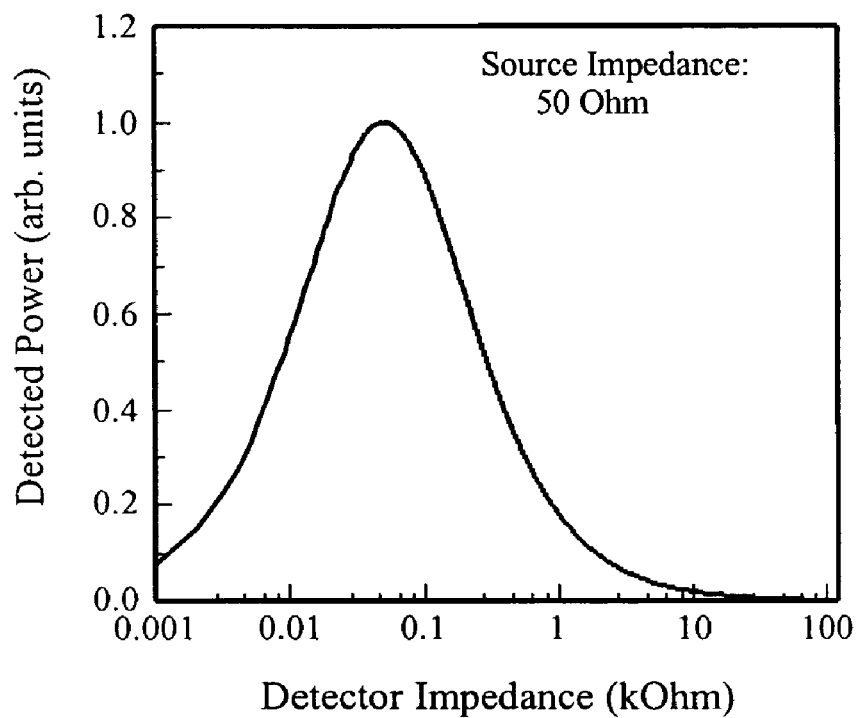
FIG. 2 illustrates how the detected power depends on the impedance matching between a 50-Ω source and the detector input impedance.

According to an embodiment of the present invention, an acoustic detector based on rupture event scanning ("REVS") with a detection setup allowing the monitoring of REVS signals near the driving frequency and with optimized impedance matching between the REVS crystal and the front-end of the detection circuitry is provided. The acoustic detector is intended for use in detecting the presence of particles such as bacteria, viruses, or other disease-causing particulates in liquid samples with extreme high sensitivity.

The acoustic detector according to an embodiment of the present invention works with a method that comprises the steps of providing a piezo-electric crystal that is able to exhibit resonant mechanical vibrations at certain frequencies, and that has at least one surface that is designed so that said particles in said liquid would bind to said at least one surface; bringing said at least one surface in contact with said liquid comprising said particles; driving said crystal into mechanical vibration with a sinusoidal electrical driving signal at a frequency slightly above the fundamental series resonance frequency of said crystal; connecting said crystal with the first input of a balanced comparator circuitry of low input impedance; providing a sinusoidal amplitude- and phase-adjustable cancellation signal at said frequency to the second input of said balanced comparator circuitry; detecting a sinusoidal output signal at said frequency at the output of said balanced comparator circuitry; adjusting the amplitude and phase of said cancellation signal so that said sinusoidal output signal at the output of said balanced comparator circuitry is cancelled out; increasing the amplitudes of said driving signal and said cancellation signal proportional to each other; detecting transient signals at the output of said balanced circuitry; and deriving the conclusion that particles comprised in said liquid had bound to said surface of said crystal from the detection of said transient signals.

The method according to an embodiment of the present invention, and apparatus to reduce the method to practice, will now be described in more detail. As in REVS detectors of prior art, a piezo-electric crystal that is able to exhibit resonant mechanical vibrations at certain frequencies is used. At least one surface of the crystal is prepared so that disease-causing particles in a liquid sample will bind to the crystal surface, when the liquid sample is brought into contact with the crystal. In an example, a crystal surface can be "activated" by attaching antibodies to it, using methods known in the art. If a liquid sample, comprising disease-causing "binding partners" to the antibodies, is brought into contact with the activated surface of the crystal, these binding partners will form binding complexes with the antibodies at the surface.

In order to detect the presence of such binding complexes, the REVS crystal is, as in REVS detectors of prior art, brought into vibration by applying an RF electric field via thin conducting electrodes attached to two opposite faces of the crystal. A typical REVS crystal is an AT-cut quartz crystal of 8 mm diameter and approximately 100-μm thickness, with electrodes of 4 mm diameter, attached centrally to the two faces.

Figure 3:
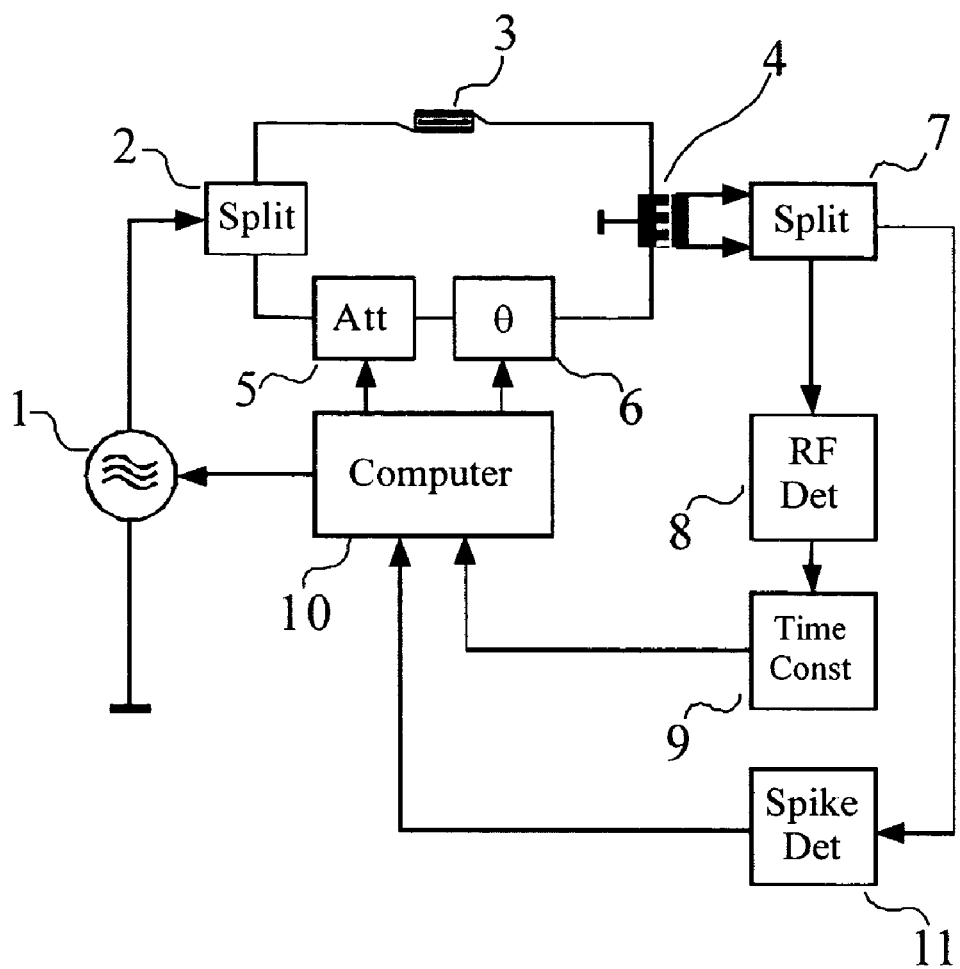
FIG. 3 illustrates schematically a first detection setup for an acoustic detector according to an embodiment of the present invention.

The electronic setup of an acoustic detector according to an embodiment of the present invention, and its electronic mode of operation, differ totally from REVS based detectors of prior art. A first detection setup for an acoustic detector according to an embodiment of the present invention is illustrated in FIG. 3. In the setup of FIG. 3, the output of a signal source (1) for a sinusoidal electrical RF signal is connected to the input of a first signal splitting device (2), e.g. a "Magic T" in coaxial design. Preferably, signal-splitting device (2) contains also elements that provide a certain attenuation in both of its output channels. A first output of splitting device (2) is connected to one electrode of a resonant crystal (3). The second electrode of crystal (3) is connected to a first input of a transformer (4) of relatively low input impedance having a center-tapped primary coil. The center tap of said primary coil is connected to ground potential.

The second output of splitting device (2) is connected to the input of a computer-controlled attenuator (5), the output of which is in turn fed to the input of a computer-controlled phase shifter (6). It will be understood that, in an acoustic detector according to an embodiment of the present invention, the order of arranging attenuator (5) and phase shifter (6) could be reversed without any negative effect on the operational principle. The output of phase shifter (6) is connected with the second input of transformer (4), providing a cancellation signal at the same frequency as the driving signal. The secondary coil of transformer (4) is connected with the input of a second signal splitting device (7), similar in design to the first signal splitting device (2). One output of signal splitting device (7) is connected with the input of a sensitive RF voltmeter (8), whereby voltmeter (8) can be a narrow-band instrument. The output signal of RF voltmeter (8) is connected to a low-pass filter (9) having a selectable time constant. The output of low-pass filter (9) is connected with a computer (10). In a modification of a setup according to an embodiment of the present invention, the function of low-pass filter (9) can be performed within computer (10) by applying software that performs digital filtering operations.

In the setup of FIG. 3, attenuator (5) and phase shifter (6) both have control inputs that are connected with computer (10). The second output of signal splitting device (7) is connected with the input of a "spike detector" (11). This is an electronic circuitry having an adjustable threshold level. Spike detector (11) generates a voltage at its output, whenever a signal larger than the adjusted threshold level reaches its input. Spike detector (11) is also designed so that the amplitude of the generated output signal is proportional to the amplitude of the input signal. Spike detector (11) can be an ultra-fast broad-band device, or can be equipped with tunable frequency filters. In general, spike detector (11) can produce its output signal either in analog or in digital format. The output of spike detector (11) is connected with computer (10). Finally, computer (10) is also connected with a control input of signal source (1) for controlling the output amplitude and the frequency of signal source (1).

In operation, attenuator (5) is adjusted by computer (10) to a high attenuation value. Signal source (1) is set on a relatively low output level, and the frequency is tuned over a frequency range comprising the fundamental series resonance frequency, $f_s$, of crystal (3). Due to the high attenuation of attenuator (5), RF voltmeter (8) monitors a conductivity resonance spectrum of crystal (3) that is recorded in computer (10). Computer (10) calculates an optimum driving frequency $f_{opt} > f_s$ by determining the frequency $f_{opt}$ at which the first derivative of the magnitude of the conductivity resonance spectrum has its maximum negative value. In a next step, computer (10) tunes signal source (1) to the optimum driving frequency $f_{opt}$. Due to the high attenuation value of attenuator (5), RF voltmeter (8) will, in this case, detect a signal of frequency $f_{opt}$.

Figure 4:
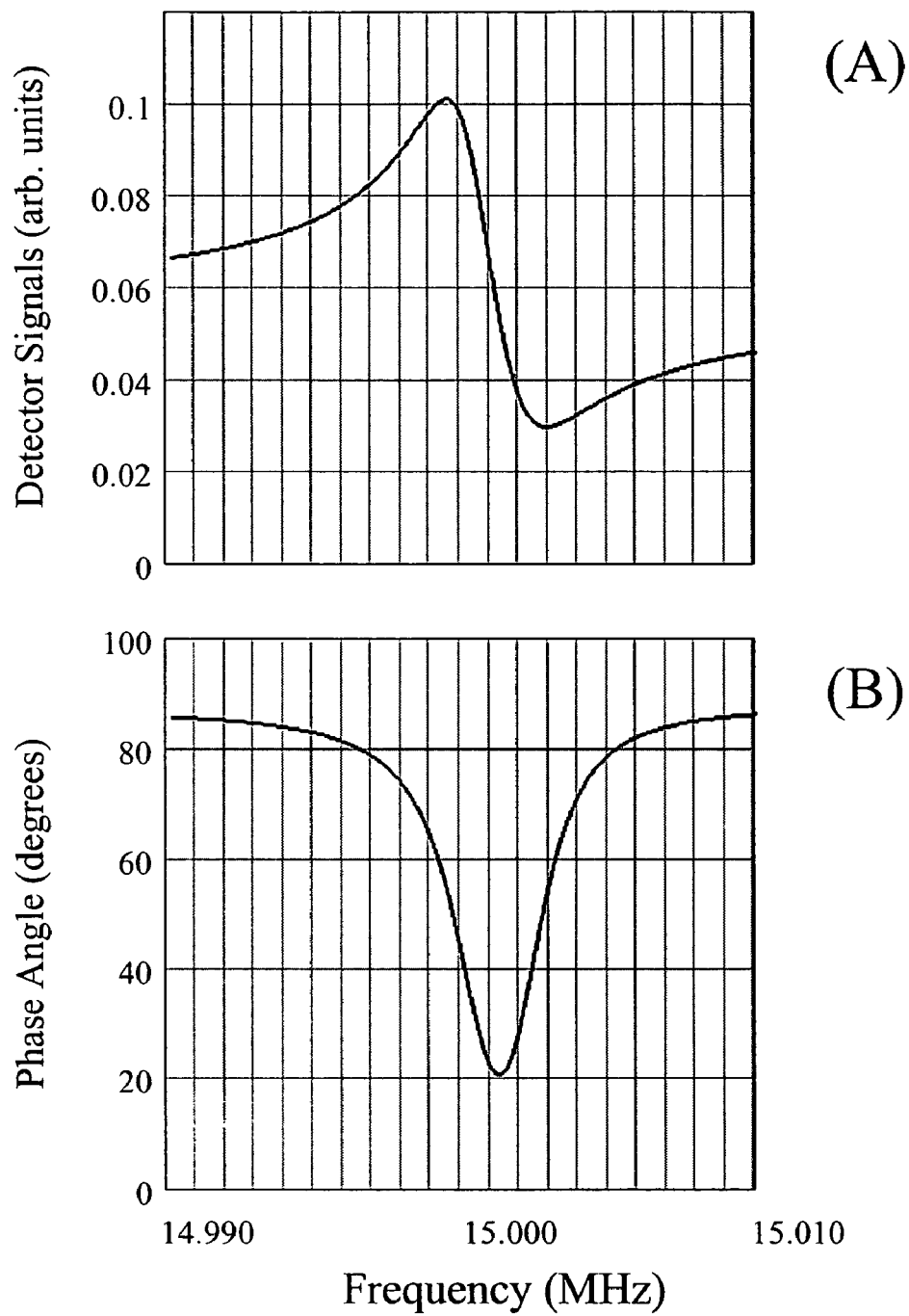
FIG. 4 shows calculated resonance spectra for the magnitude (A) and phase (B) for a REVS crystal under medium liquid loading conditions.

According to an embodiment of the present invention, computer (10) adjusts now in a periodic step-wise sequence the attenuation of attenuator (5) and the phase shift within phase shifter (6) to such values that result in lower and lower signal amplitudes as detected by RF voltmeter (8). When a zero RF signal amplitude is reached, then the attenuation and phase shift values are identical to the attenuation and phase shift values within crystal (3). FIG. 4 shows, as an example, how the signal magnitude and phase behind crystal (3) at the first input to transformer (4) depend on the frequency. These curves have been calculated for a 15-MHz crystal, assuming medium liquid loading due to a liquid sample that is in contact with the crystal. FIG. 4A shows the magnitude of the conductivity resonance spectrum, and FIG. 4B shows the phase angle of the conductivity resonance spectrum.

Once the attenuation within attenuator (5) and phase shift within phase shifter (6) match exactly with the corresponding crystal values, the RF input signal at RF voltmeter (8), and, of course, the output signal of low-pass filter (9) that is fed towards computer (10) will be equal to zero. A relatively high precision in this "nulling" procedure can be achieved by selecting an appropriate time constant for low-pass filter (9). It has to be emphasized that the "nulling" will be stable over time due to the still active closed-loop feedback circuit involving devices (5), (6), (4), (7), (8), (9), and (10), and also due to the fact that the driving signal and the cancellation signal are derived from the same signal source. Due to the latter, any small drift in the signal sources' amplitude, frequency, or phase is automatically cancelled out. Within said closed-loop feedback circuit, transformer (4) is called a "balanced comparator circuitry".

After setting signal source (1) to $f_{opt}$, and after performing a successful nulling procedure as described above, the signal amplitude of signal source (1) is slowly increased over time in a ramp-like fashion. This measure will not cause any non-zero RF signal at the RV voltmeter input due to the complete cancellation between the two signals arriving at the two inputs of transformer (4) as a consequence of the still active closed-loop feedback circuit.

If, at an increased driving level in an acoustic detector according to an embodiment of the present invention, binding complexes between binding partners that are present at crystal (3) break apart from the crystal surface, then the so-called "mass loading" of the crystal is also changing suddenly, and short transient signals will be generated at the output of transformer (4). This is so because the breaking away of binding complexes results in sudden changes in the attenuation and phase shift of the driving signal within crystal (3). This, in turn, causes an imperfect cancellation between the two signals arriving at transformer (4), and in the generation of an electric transient signal. The transient signal contains a whole spectrum of frequencies near the driving frequency, whereby the exact shape and the width of the spectrum will depend on the nature of the breaking-apart process. Experiments have revealed frequency components within a range of 170 kHz below and above the driving frequency, but even wider ranges such as 300 kHz can be expected. The arrangement of splitting device (2) and resonant piezo-electric body (3), together with attenuator (5) and phase shifter (6), are referred to as a "transient signal isolation circuit."

When a transient signal is generated due to the breaking away of binding complexes from the crystal surface, spike detector (11) will receive such transient signals, and will send a corresponding output signal towards computer (10). In this way, the acoustic detector allows for the detection of binding complexes, and, therefore, the detection of the presence of disease-causing particles in the liquid sample. Due to the fact that in an apparatus according to an embodiment of the present invention the output amplitude from spike detector (11) is proportional to the amplitude of the transient signal received at the input, information regarding the number of broken binding complexes can be obtained. This allows to determine not only the presence of disease-causing particles within the liquid sample, but also to determine the concentration of particles.

Transient signals of all shapes and at all frequencies can be detected if an ultra-fast broad-band spike detector is used. It is, however, also possible to use a spike detector equipped with tunable frequency filters. In this case, an improved detectivity may be achieved thanks to reduced noise levels. It has to be emphasized that, due to the total cancellation of the driving signal at frequency $f_{opt}$ at transformer (4), spike detector (11) could be made sensitive in particular to transient signals with frequency components close to the driving frequency by using appropriate frequency filters. This important feature is missing in REVS detectors of prior art. Since the transient signals near $f_{opt}$ are likely to be much larger than transient signals near the third harmonic of the crystal, a significantly improved detection sensitivity for disease-causing particles can be expected for an acoustic detector according to an embodiment of the present invention.

Figure 5:
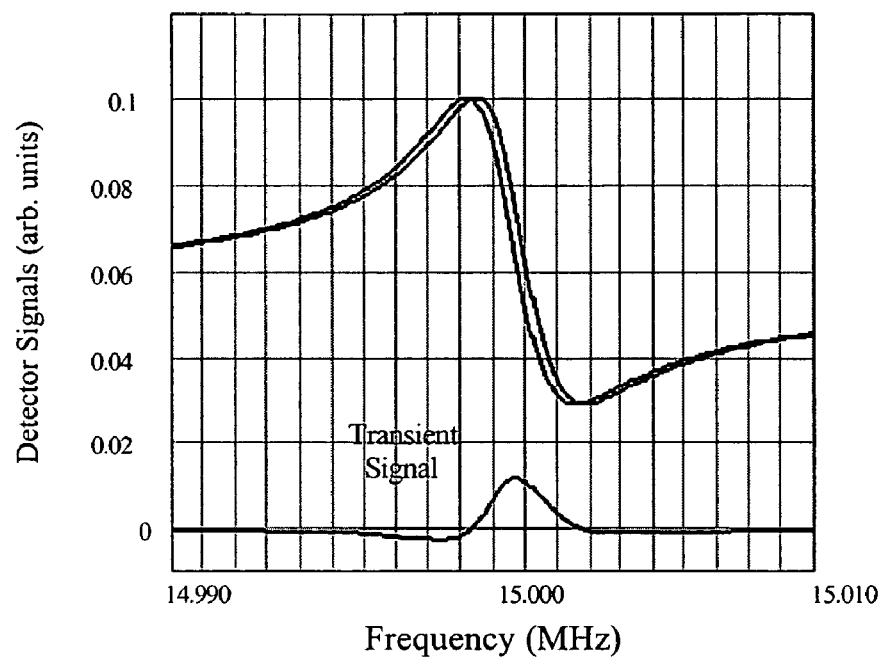
FIG. 5 shows two simulated conductivity magnitude spectra, before and after a small change in the mass loading and also shows the change in conductivity as a function of the driving frequency.

FIG. 5 shows two simulated conductivity magnitude resonance spectra for a 15-MHz crystal under medium liquid loading. The spectrum slightly more to the left corresponds to the mass loading before, and the spectrum slightly more to the right corresponds to the mass loading after the breaking away of binding complexes. FIG. 5 also shows the change in conductivity as a function of the driving frequency, referred to as "Transient Signal". When a crystal is operated at any frequency within the resonance region in a measuring setup that is responsive to the crystal's conductivity magnitude, any change in mass loading is expected to generate a permanent change in the measured conductivity at that frequency. A sudden change in the mass loading, however, is expected to generate a transient signal that is much larger than the expected permanent change in the conductivity signal.

Under the assumption, that the amplitude of the transient signal is proportional to the small change in conductivity magnitude experienced at the driving frequency, an inspection of FIG. 5 indicates that driving the crystal exactly at its fundamental series resonance frequency, $f_s$, may not be an optimum. FIG. 5 can be interpreted in fact so that there should be no observable transient signal in this case. One could say that, when driven exactly at the fundamental series resonance frequency, the crystal can "flip" from the first state into the second state without observable change in conductivity magnitude. In other words, at that frequency, a change in mass loading does not change the measured conductivity value.

The plots in FIG. 5 suggest that, according to an embodiment of the present invention, a REVS crystal should be operated at a frequency slightly above the fundamental series resonance frequency in order to generate a maximum REVS transient signal. The optimum frequency, $f_{opt}$, is located at the (negative) maximum of the first derivative of the conductivity magnitude spectrum, with $f_{opt} > f_s$. In practice, and as already described above, one would record one such conductivity spectrum under the actual liquid loading conditions, and determine the frequency of maximum negative slope to obtain the frequency $f_{opt}$.

As has been mentioned above, transformer (4) in FIG. 3 has a low input impedance. Therefore, improved impedance matching between the REVS crystal and the front-end of the detection circuitry is achievable, compared to REVS devices of the prior art. Consequently, maximum transient signal power can be extracted out of crystal (3). This represents a significant improvement over REVS detectors of prior art, where the front-end of the detection electronics facing the crystal has, out of necessity, always been a high-impedance circuitry. The necessity resulted from the fact that an electrical parallel resonance circuit with a resonance frequency near the third harmonic of the crystal was required to filter out the driving signal near the fundamental resonance frequency.

Figure 6:
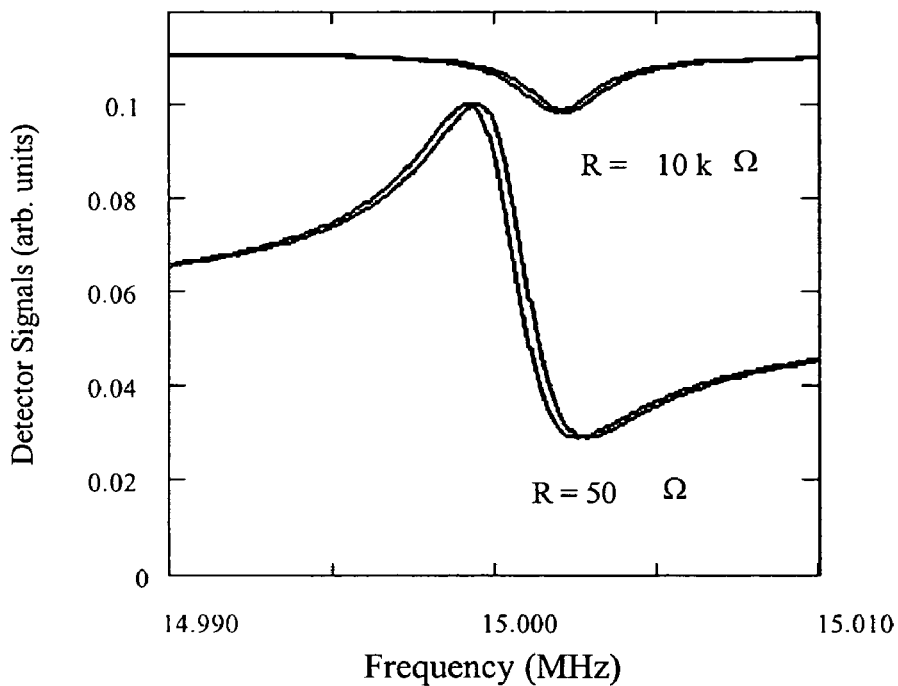
FIG. 6 shows simulated conductivity magnitude spectra as in FIG. 5, but for high-impedance (R=10 kΩ) and low-impedance (R=50Ω) out-coupling conditions.
Figure 7:
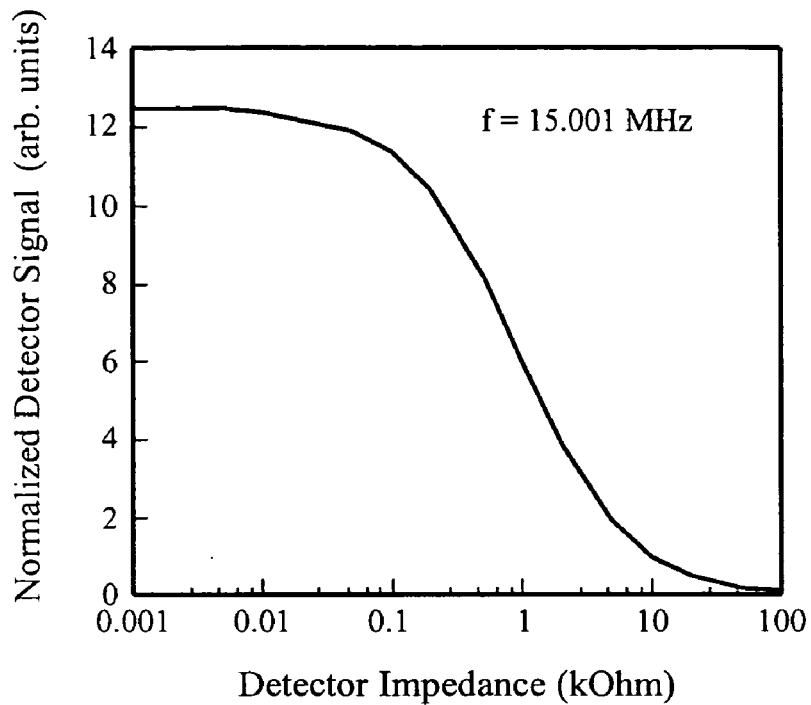
FIG. 7 illustrates calculations for a normalized detector signal from a 50-Ω REVS crystal versus the detector input impedance.

FIG. 6 illustrates two pairs of simulated conductivity magnitude resonance spectra, each of them before and after the breaking away of binding complexes. One of the pairs of spectra relates to the out-coupling into a high-impedance (10 kΩ) circuitry, and one relates to the out-coupling into a low-impedance (50 Ω) circuitry. It becomes obvious from FIG. 6 that coupling into a high-impedance network will result in a much lower relative change in the observed conductivity, and, consequently, in a transient signal that resides on top of a much larger signal. This statement is illustrated in FIG. 7 showing calculations for a "Normalized Detector Signal" extracted from a REVS crystal versus the "Detector Impedance" of the front-end electronics. Normalization was applied in dividing the change in signal by the start value of the signal. As in FIG. 6, a crystal with a series resonance frequency slightly below 15 MHz, and an optimum driving frequency slightly above 15 MHz have been assumed.

Figure 8:
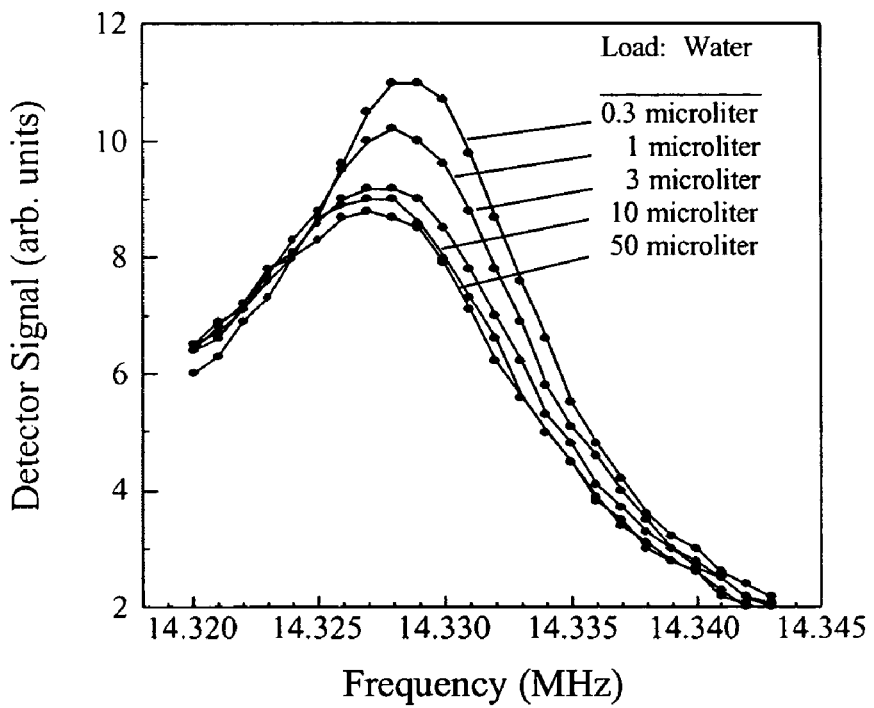
FIG. 8 illustrates measurements of conductivity magnitude resonance spectra on a 14.3-MHz REVS crystal under varying liquid loading conditions.
Figure 9:
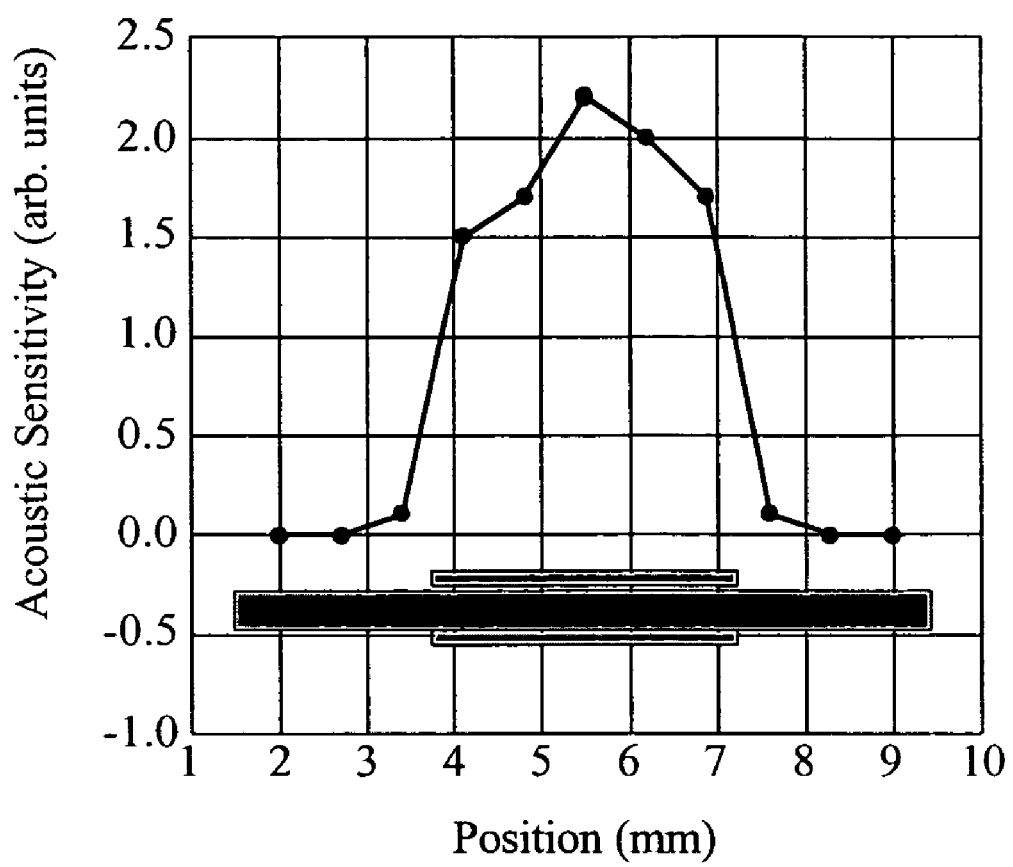
FIG. 9 shows the acoustic sensitivity measured across a 14.3-MHz quartz crystal of 8 mm diameter with centrally located electrodes of approximately 4 mm diameter.

The plots shown in FIG. 8 represent experimental data on conductivity magnitude resonance spectra obtained on a 14.3-MHz REVS crystal for varying liquid loading conditions. The crystal had a diameter of 8 mm and was equipped with centrally located electrodes of 4 mm diameter. Water droplets with a volume between 0.3 μL and 50 μL have been loaded centrally onto the crystal surface. As can be seen, increased water loading causes stronger "damping" and a shift of the conductivity maximum towards lower frequencies, but at larger droplet volume the increase in the damping efficiency becomes less pronounced. FIG. 9 illustrates results of experiments aiming at the measurement of the same crystal's spatial sensitivity. In this case, water droplets of 0.1-μL volumes have been disposed onto the crystal surface in a serial mode along a diameter-path across the crystal. FIG. 9 indicates also the 8-mm crystal carrying the 4-mm gold electrode. As can be seen, the acoustic sensitivity is limited essentially to the electrode area. Only a minor fringe effect is observed just outside of the electrode area.

The behavior illustrated in FIG. 9 is very plausible because the electric field generating the acoustic vibrations is highly limited to the electrode area, given the relatively small crystal thickness (0.117 mm). The experiment described above allows drawing one important conclusion. When designing REVS-based assay devices for the detection of very low target numbers (e.g. <10), binding partners that attract targets are preferably deposited only onto the electrode area. If the whole crystal surface is being "activated" to capture targets, the assay's detectivity drops significantly. In the current crystal (and in devices as published), only 25% of the crystal surface is occupied by the electrodes. If, for example, a liquid sample contains only ten (10) targets, 7–8 of them would bind with partners outside of the electrode area, and would be unable to contribute to the transient REVS signal. In other words, the chances to detect all of the ten present targets would drop down to 20–30%. With fewer target numbers, no detection at all may be achieved. The less pronounced increase in damping as seen in FIG. 8 for higher droplet volume results from the fact that in this case the droplet covers more surface area than occupied by the electrodes. In other words, the surface area covered by the droplet includes regions with no sensitivity.

Figure 10:
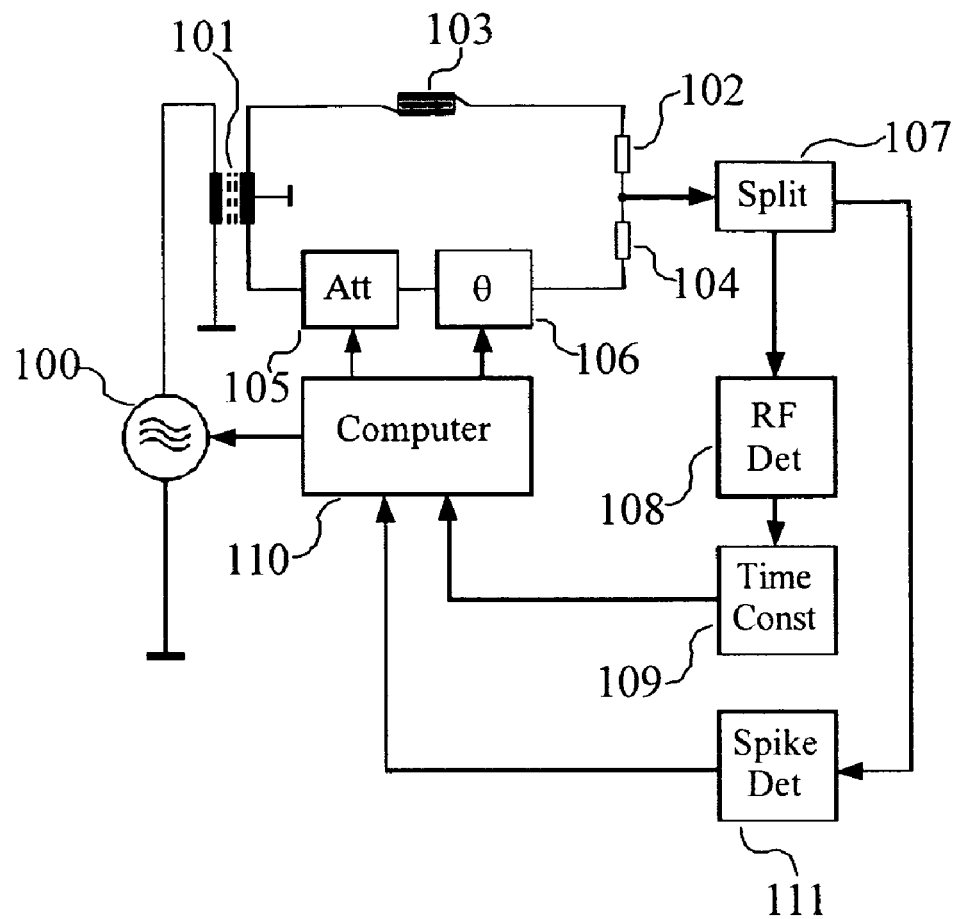
FIG. 10 illustrates schematically a modification of a detection setup for an acoustic detector according to an embodiment of the present invention.

FIG. 10 illustrates a possible modification of an acoustic detector according to an embodiment of the present invention. In the setup of FIG. 10, the output of a signal source (100) for a sinusoidal electrical RF signal is connected to the primary coil of a transformer (101) having a center-tapped secondary coil. The center tap of said secondary coil is connected to ground potential. One end of said secondary coil of transformer (101) is connected to one electrode of a resonant crystal (103). The second electrode of crystal (103) is connected to one end of a resistor (102) of two resistors that are connected in series. The two resistors have relatively low impedance, e.g. 50Ω, in order to allow for optimum impedance matching conditions with said crystal (103).

The second end of said secondary coil of transformer (101) is connected to the input of a computer-controlled attenuator (105), the output of which is in turn fed to the input of a computer-controlled phase shifter (106). The output of phase shifter (106) is connected with the end of a second resistor (104) of said two resistors in series. The joining point of resistors (102) and (104) is connected with the input of a signal splitting device (107), similar in design to the signal splitting devices (2) and (7) in FIG. 3. One output of signal splitting device (107) is connected with the input of a sensitive RF voltmeter (108), whereby voltmeter (108) can be a narrow-band instrument. The output signal of RF voltmeter (108) is connected to a low-pass filter (109) having a selectable time constant. The output of low-pass filter (109) is connected with a computer (110). In a modification of a setup according to an embodiment of the present invention, the function of low-pass filter (109) can be performed within computer (110) by applying software that performs digital filtering operations.

In the setup of FIG. 10, attenuator (105) and phase shifter (106) both have control inputs that are connected with computer (110). The second output of signal splitting device (107) is connected with the input of a "spike detector" (111). This is an electronic circuitry having an adjustable threshold level. Spike detector (111) generates a voltage at its output, whenever a signal larger than the adjusted threshold level reaches its input. Spike detector (111) is also designed so that the amplitude of the generated output signal is proportional to the amplitude of the input signal. Spike detector (111) can be an ultra-fast broad-band device, or can be equipped with tunable frequency filters. In general, spike detector (111) can produce its output signal either in analog or in digital format. The output of spike detector (111) is connected with computer (110). Finally, computer (110) is also connected with a control input of signal source (100) for controlling the output amplitude and the frequency of signal source (100).

In operation, attenuator (105) is adjusted by computer (110) to a high attenuation value. Signal source (100) is set on a relatively low output level, and the frequency is tuned over a frequency range comprising the fundamental series resonance frequency, $f_s$, of crystal (103). Due to the high attenuation of attenuator (105), RF voltmeter (108) is monitoring a conductivity resonance spectrum of crystal (103) that is recorded in computer (110). Computer (110) calculates an optimum driving frequency $f_{opt} > f_s$ by determining the frequency $f_{opt}$ at which the first derivative of the magnitude of the conductivity resonance spectrum has its maximum negative value. In a next step, computer (110) tunes signal source (100) to the optimum driving frequency $f_{opt}$. Due to the high attenuation value of attenuator (105), RF voltmeter (108) will, in this case, detect a signal of frequency $f_{opt}$.

According to an embodiment of the present invention, computer (110) adjusts now in a step-wise sequence the attenuation of attenuator (105) and the phase shift within phase shifter (106) to such values that result in lower and lower signal amplitudes as detected by RF voltmeter (108). When a zero RF signal amplitude is reached, then the attenuation and phase shift values are identical to the attenuation and phase shift values within crystal (103).

Once the attenuation within attenuator (105) and phase shift within phase shifter (106) match exactly with the corresponding crystal values, the RF input signal at RF voltmeter (108), and, of course, the output signal of low-pass filter (109) that is fed towards computer (110) will be equal to zero. A relatively high precision in this "nulling" procedure can be achieved by selecting an appropriate time constant for low-pass filter (109). As in the first apparatus according to an embodiment of the present invention, the "nulling" will be stable over time due to the closed-loop feedback circuit involving devices (105), (106), (102), (104), (107), (108), (109), and (110). Within said closed-loop feedback circuit, the two resistors in series, (102) and (104), are called a "balanced comparator circuitry".

After setting signal source (100) to $f_{opt}$, and after performing a successful nulling procedure as described above, the signal amplitude of signal source (100) is slowly increased over time in a ramp-like fashion. This measure will not cause any non-zero RF signal at the RV voltmeter input due to the complete cancellation at the joining point of said two resistors (102) and (104) between the two signals arriving at the two ends of resistors (102) and (104), respectively. If, however, binding complexes between binding partners that are present at crystal (103) suddenly break apart from the crystal surface, then the mass loading of the crystal also changes suddenly, and transient signals will be generated at the joining point of resistors (102) and (104). This is so because the breaking away of binding complexes results in sudden changes in the attenuation and phase shift of the driving signal within crystal (103). This, in turn, causes an imperfect cancellation between the two signals arriving at the ends of resistors (102) and (104), and, consequently, in the generation of an electric transient signal.

When a transient signal is generated due to the breaking away of binding complexes from the crystal surface, spike detector (111) will receive such transient signals, and will send a corresponding output signal towards computer (110). In this way, the acoustic detector allows for the detection of binding complexes, and, therefore, the detection of the presence of disease-causing particles in the liquid sample. Due to the fact that in an apparatus according to an embodiment of the present invention the output amplitude from spike detector (111) is proportional to the amplitude of the transient signal received at the input, information regarding the number of broken binding complexes can be obtained. This allows to determine not only the presence of disease-causing particles within the liquid sample, but also to determine the concentration of particles.

Figure 11:
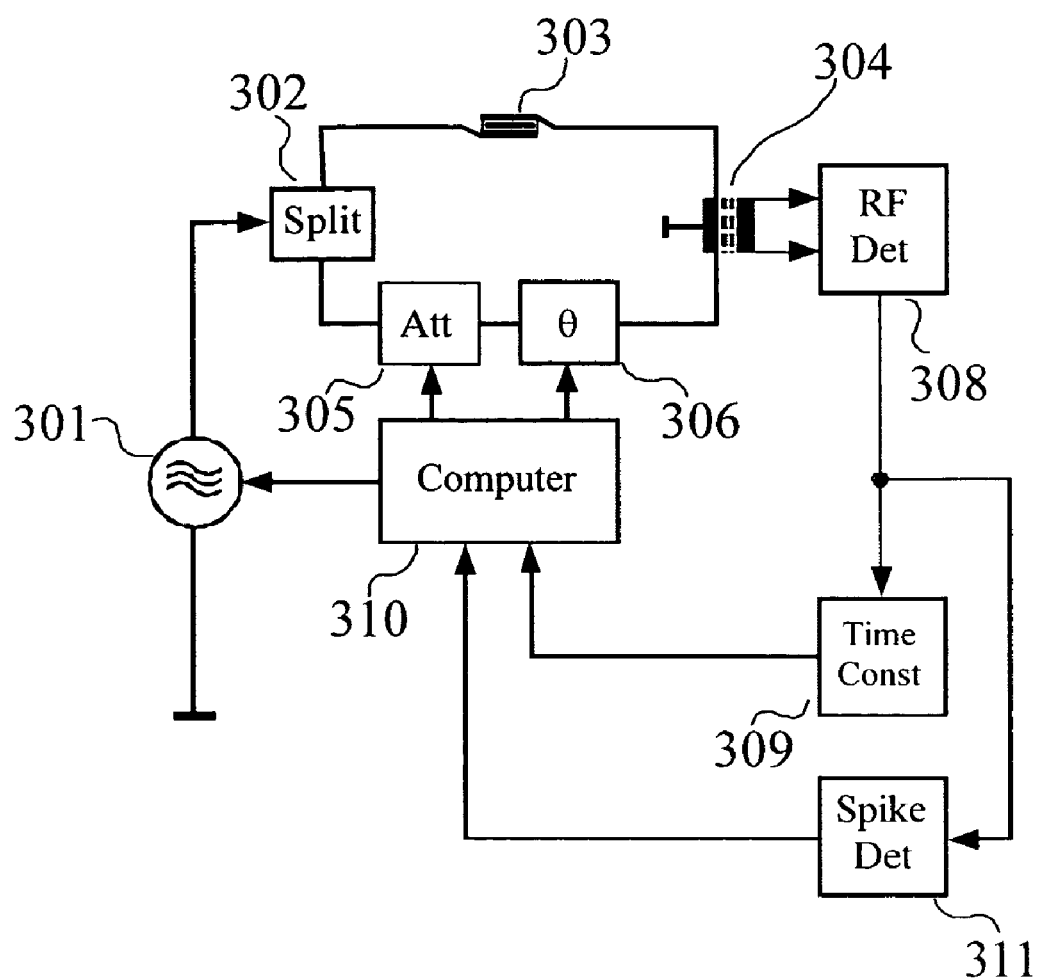
FIG. 11 shows another modification of a detection setup for an acoustic detector according to an embodiment of the present invention.

Another modification of an acoustic detector according to an embodiment of the present invention is illustrated in FIG. 11. The setup in FIG. 11 is very similar to the one shown in FIG. 3, with a signal source (301), a splitting device (302), a crystal (303), a computer-controlled attenuator (305), and a computer-controlled phase shifter (306). In this modified arrangement, the output of transformer (304) is directly connected with the input of an RV voltmeter (308). As in the arrangement of FIG. 3, the output of RF voltmeter (308) is connected to a low-pass filter (309) having a selectable time constant, and the output of low-pass filter (309) is connected to computer (310). In contrast to the arrangement in FIG. 3, the output of RF voltmeter (309) is also connected to a spike detector (311), and the output of spike detector (311) is connected with computer (310). Spike detector (311) has features as described already for spike detector (11) in FIG. 3. In principle, it would be possible to integrate the functions performed by low-pass filter (309) and spike detector (311) into RF voltmeter (308).

Figure 12:
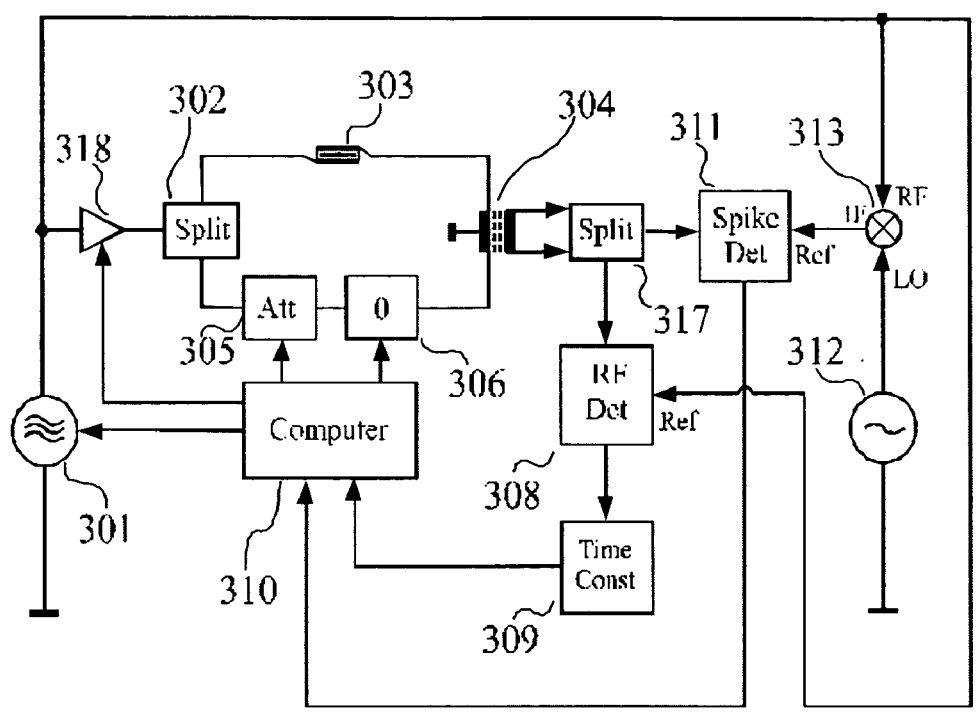
FIG. 12 illustrates a further modification of a detection setup for an acoustic detector according to an embodiment of the present invention.

A further modification of an acoustic detector according to an embodiment of the present invention is shown in FIG. 12. This arrangement corresponds highly with the arrangements illustrated in FIGS. 3 and 11, with the exception that RF detector (308) is now a first synchronous detector such as a lock-in amplifier. Due to the fact that RF detector (308) receives its reference signal directly from signal source (301), said RF detector is tuned to the driving frequency $f_{opt}$ of signal source (301). Part of the signal from signal source (301) is directed towards the RF input of an electronic mixer (313), where the signal is mixed with a low-frequency offset signal coming from an offset generator (312) towards the LO input of mixer (313). The IF output of mixer (313) is connected with the reference input of spike detector (311), carrying a reference signal that is shifted in frequency away from the driving frequency $f_{opt}$. In the setup of FIG. 12, a second synchronous detector such as a lock-in amplifier is used as spike detector (311), but with a very short time constant so that it is able responding to short transient signals. By selecting different offset frequencies for offset generator (312), transient signals at different frequencies near the high frequency $f_{opt}$ of signal source (301) can be detected with high sensitivity. Mixer (313) is preferably a single-sideband modulator. As in the setup of FIG. 3, a splitting device (317) is arranged immediately after transformer (304).

In the setup shown in FIG. 12, an amplifier of variable gain (318) is inserted into the path between signal source (301) and splitting device (302). The gain in amplifier (318) is controlled by computer (310) in order to increase the driving signal amplitude for crystal (303) over time. The introduction of variable-gain amplifier (318) allows to keep the signal output amplitude of signal source (301) at a constant level, which is advantageous with respect to the reference signals for both synchronous detectors (308) and (311), respectively. The setup shown in FIG. 12 comprises also a computer-controlled attenuator (305), a computer-controlled phase shifter (306), and a low-pass filter (309) having a selectable time constant, whereby all three devices perform functions as in the setup shown in FIG. 11.

Figure 13:
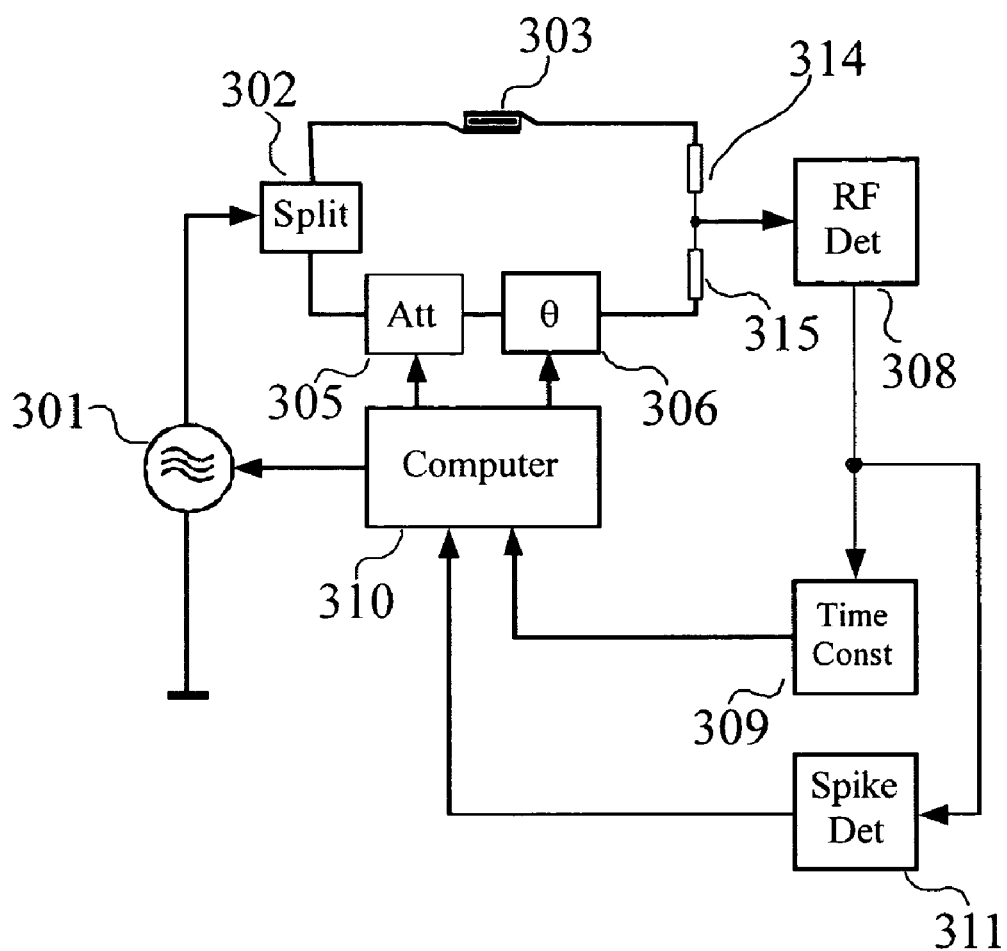
FIG. 13 illustrates a still further modification of a detection setup for an acoustic detector according to an embodiment of the present invention.

A still further modification of an acoustic detector according to an embodiment of the present invention is illustrated in FIG. 13. The setup in FIG. 13 is very similar to the one shown in FIG. 11, but in this modified arrangement, transformer (304) is replaced with two resistors (314) and (315) that are connected in series. The second electrode of crystal (303) is connected to one end of resistor (314). The output of phase shifter (306) is connected with one end of resistor (315), and the joining point of resistors (314) and (315) is connected with the input of RF voltmeter (308). All other devices shown in FIG. 13 are identical to the devices shown in FIG. 11 with the same reference numbers, and perform the same functions.

Figure 14:
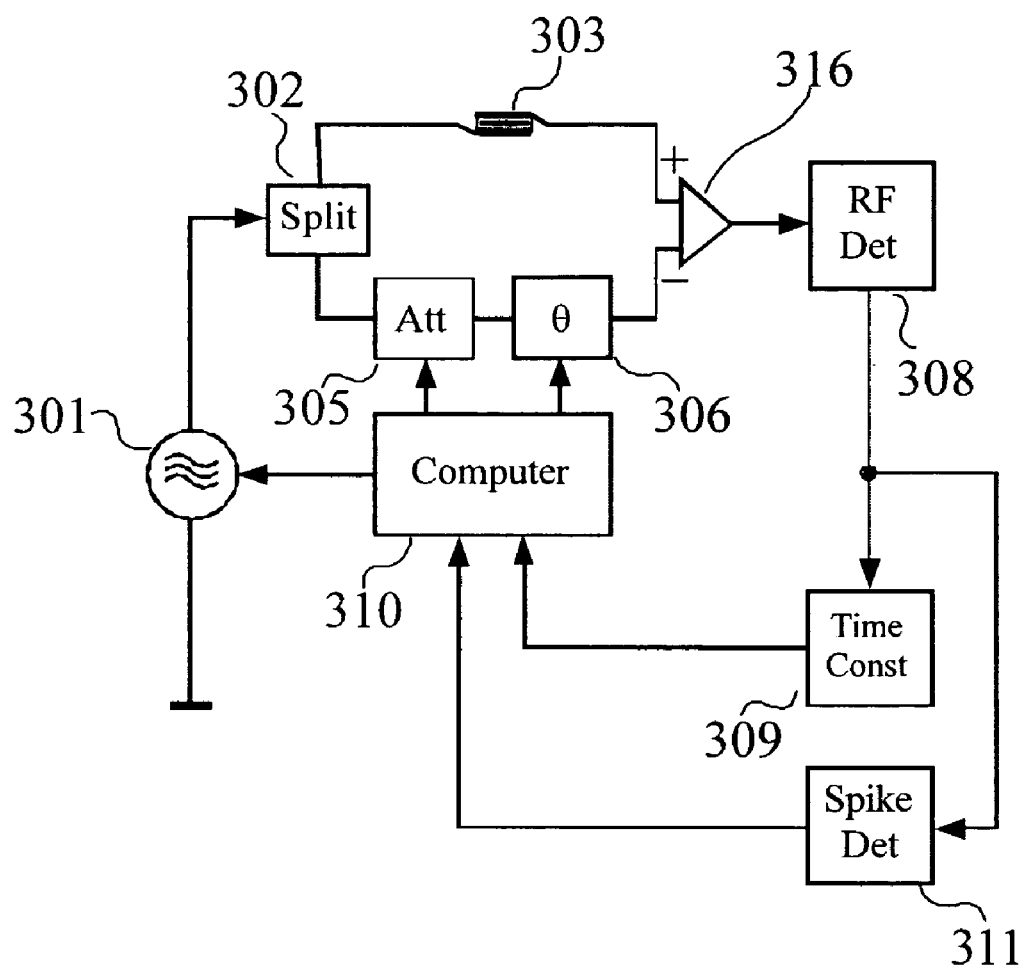
FIG. 14 illustrates another modification of a detection setup for an acoustic detector according to an embodiment of the present invention.

A final modification of an acoustic detector according to an embodiment of the present invention is illustrated in FIG. 14. The setup in FIG. 14 is also very similar to the one shown in FIG. 11, but in this modified arrangement, transformer (304) is replaced with a low-noise RF differential pre-amplifier (316). The second electrode of crystal (303) is connected to one input of pre-amplifier (316). The output of phase shifter (106) is connected with the other input of pre-amplifier (316), and the output of pre-amplifier (316) is connected with the input of RF voltmeter (308). Again, all other devices shown in FIG. 14 are identical to the devices shown in FIG. 11 with the same reference numbers, and perform the same functions.

Figure 15:
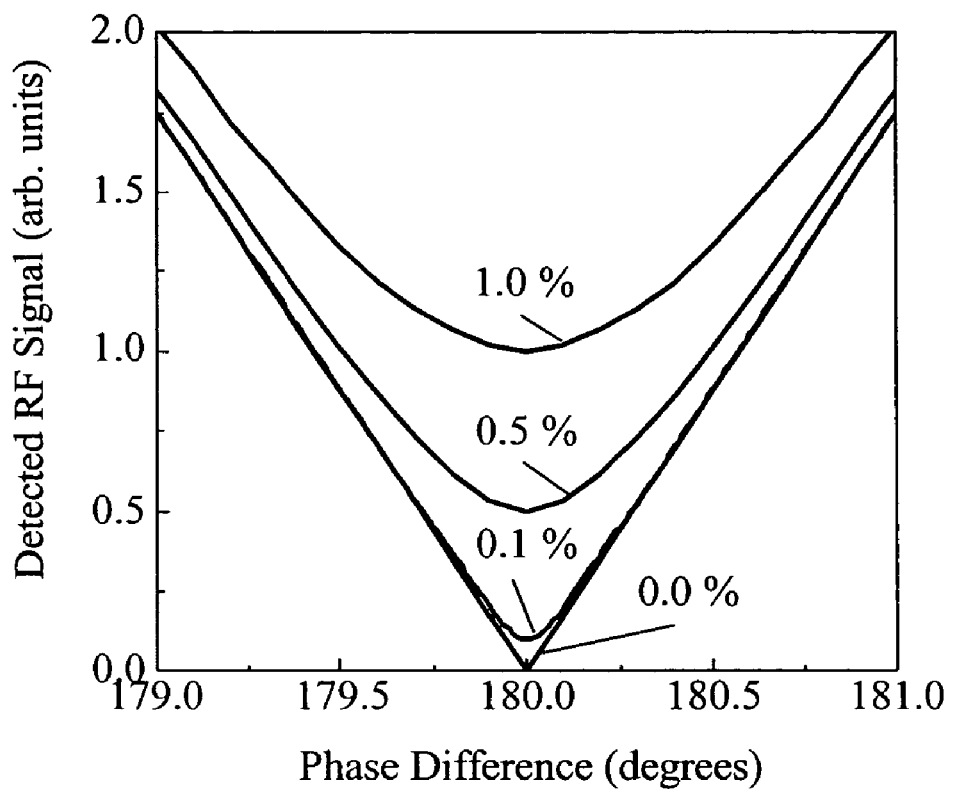
FIG. 15 shows how the amplitude of the detected RF signal depends on the exact phase and amplitude adjustment in the two channels.

In operation, the acoustic detectors shown in FIGS. 3, 10, 11, 12, 13, and 14 require a computer-controlled phase adjustment in phase shifters (6), (106), and (306) as described above. If a transformer (4) or (304) or a low-noise RF differential pre-amplifier (316) is used, the phase angle between the two signals arriving at said transformers or said pre-amplifier has to be adjusted to zero. If two resistors in series are used, the phase angle between the two signals arriving at the ends of said resistors has to be adjusted to 180 degrees. The plots in FIG. 15 show how the RF signal amplitude detected by RF voltmeters (8), (108), or (308) depend on the exact phase adjustment for the latter case. FIG. 15 shows the detected RF signal for remaining amplitude imbalances of 1.0%, 0.5%, and 0.1%, and for perfect balancing at 0.0%, respectively. As can be seen, the cancellation efficiency is increased as better amplitude balancing is performed. In the acoustic detectors shown in FIGS. 3, 10, 11, 12, 13, and 14, the combination of the RF voltmeter and the spike detector are referred to as a "transient signal detector" providing a "transient detection signal."

It was expected that for no particles attached to the crystal surface, an increase in the crystal's driving voltage would not cause any non-zero RF signal at the RV voltmeter input due to the complete cancellation between the two signals arriving at the two inputs of the "balanced comparator circuitry". Experiments have revealed, however, that quartz crystals as used in an apparatus according to an embodiment of the present invention exhibit electrical parameters that are driving voltage-dependent. The phenomenon is illustrated in FIGS. 16 to 19.

Figure 16:
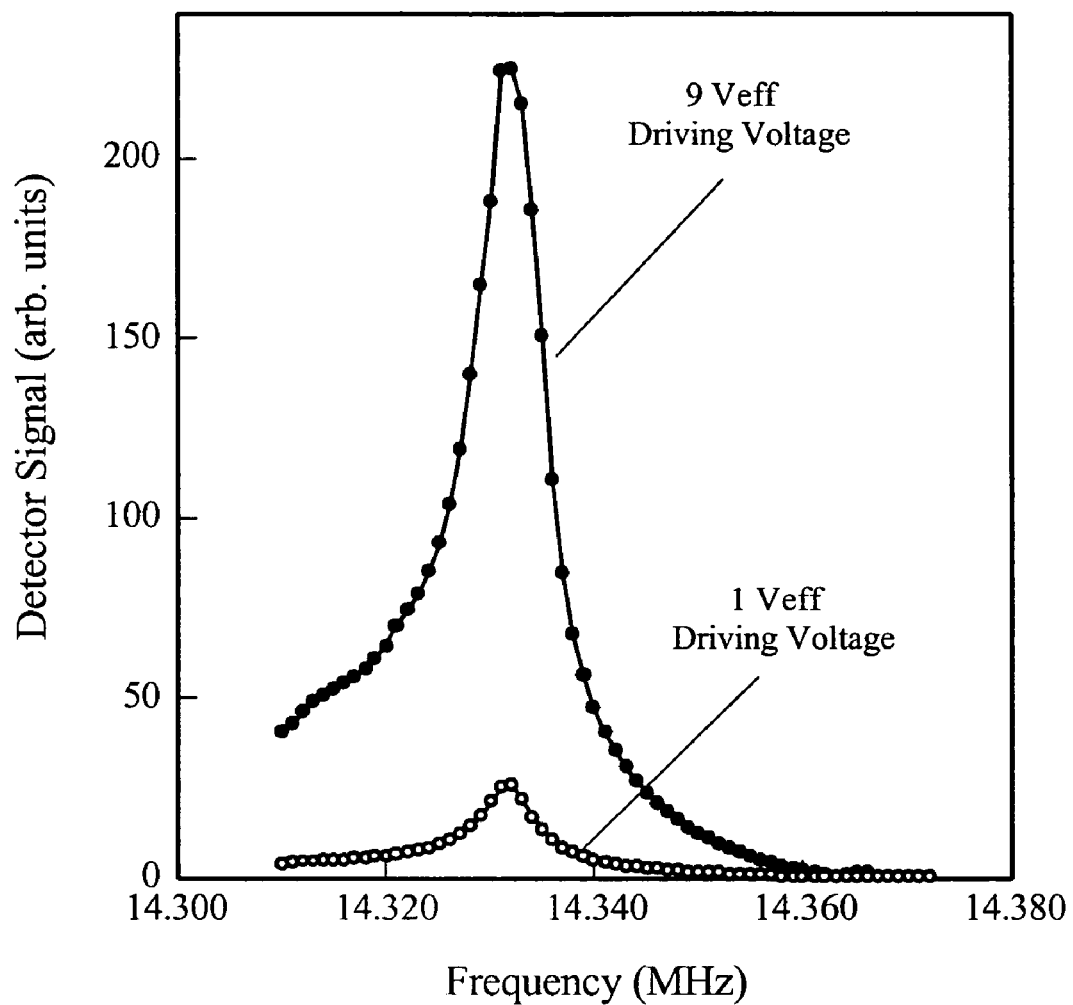
FIG. 16 depicts conductivity magnitude resonance spectra around 14.3 MHz as measured with driving signal amplitudes of 1 V and 9 V, respectively.
Figure 17:
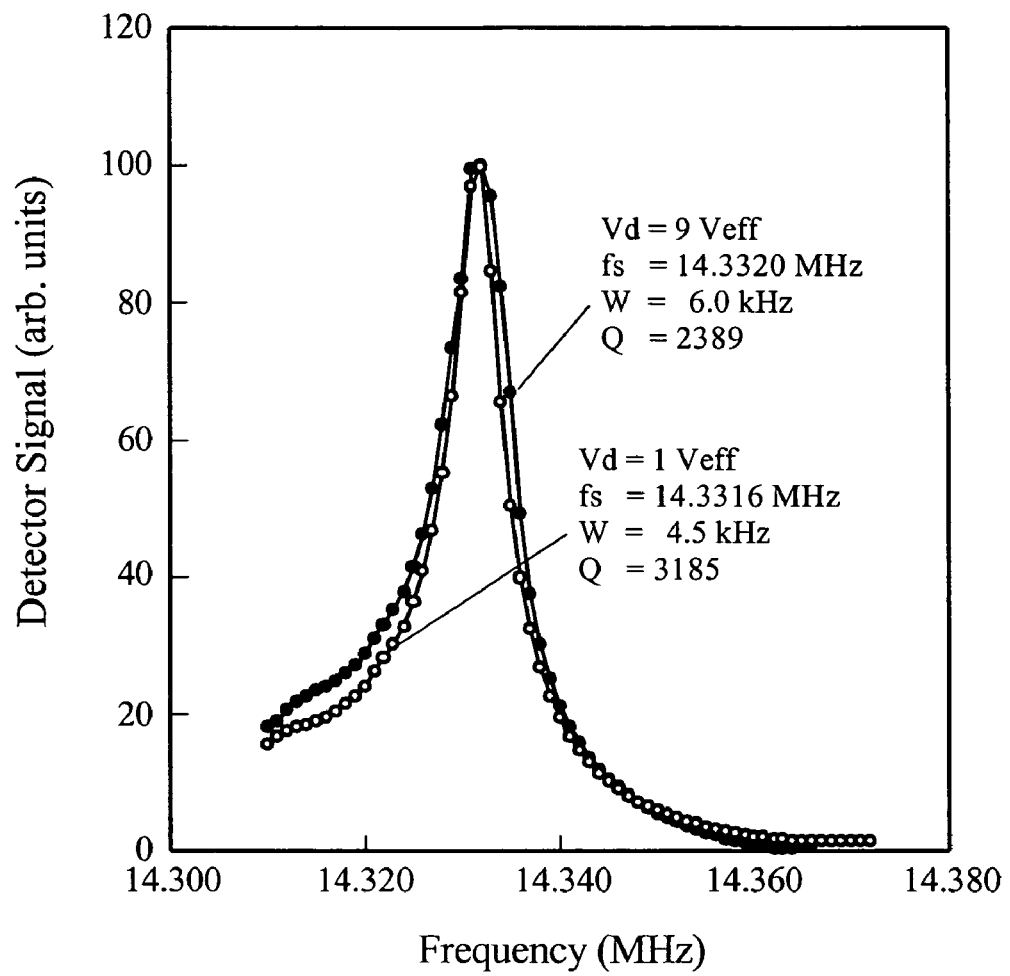
FIG. 17 shows the same two spectra as in FIG. 16, but in normalized form, allowing for comparison.

FIG. 16 depicts two conductivity magnitude resonance spectra measured on a quartz crystal of 8 mm diameter and approximately 100 μm thickness around 14.3 MHz for driving signal amplitudes of 1 V and 9 V, respectively. FIG. 17 shows the same two spectra as in FIG. 16, but in normalized form, allowing for better comparison. As can be seen, the resonance frequency is shifting by 0.4 kHz from 14.3316 MHz to 14.3320 MHz when the driving voltage is increased. The spectral width measured at 70.7% height ($=100/\sqrt{2}$) is increasing from 4.5 kHz to 6.0 kHz. Accordingly, the Q-factor decreases from 3185 to 2389 when the driving voltage is increased. The slight increase in width can be interpreted as a consequence of an increase in the crystal's ohmic resistance with increasing driving voltage. We have performed a mathematical modeling, which allows for a rough estimate of the increase in the crystal's ohmic resistance that would cause the observed widening of the resonance spectrum. According to our modeling, the ohmic resistance of the crystal would be approximately 15Ω at 1 V driving voltage, and approximately 40Ω at 9 V driving voltage.

Figure 18:
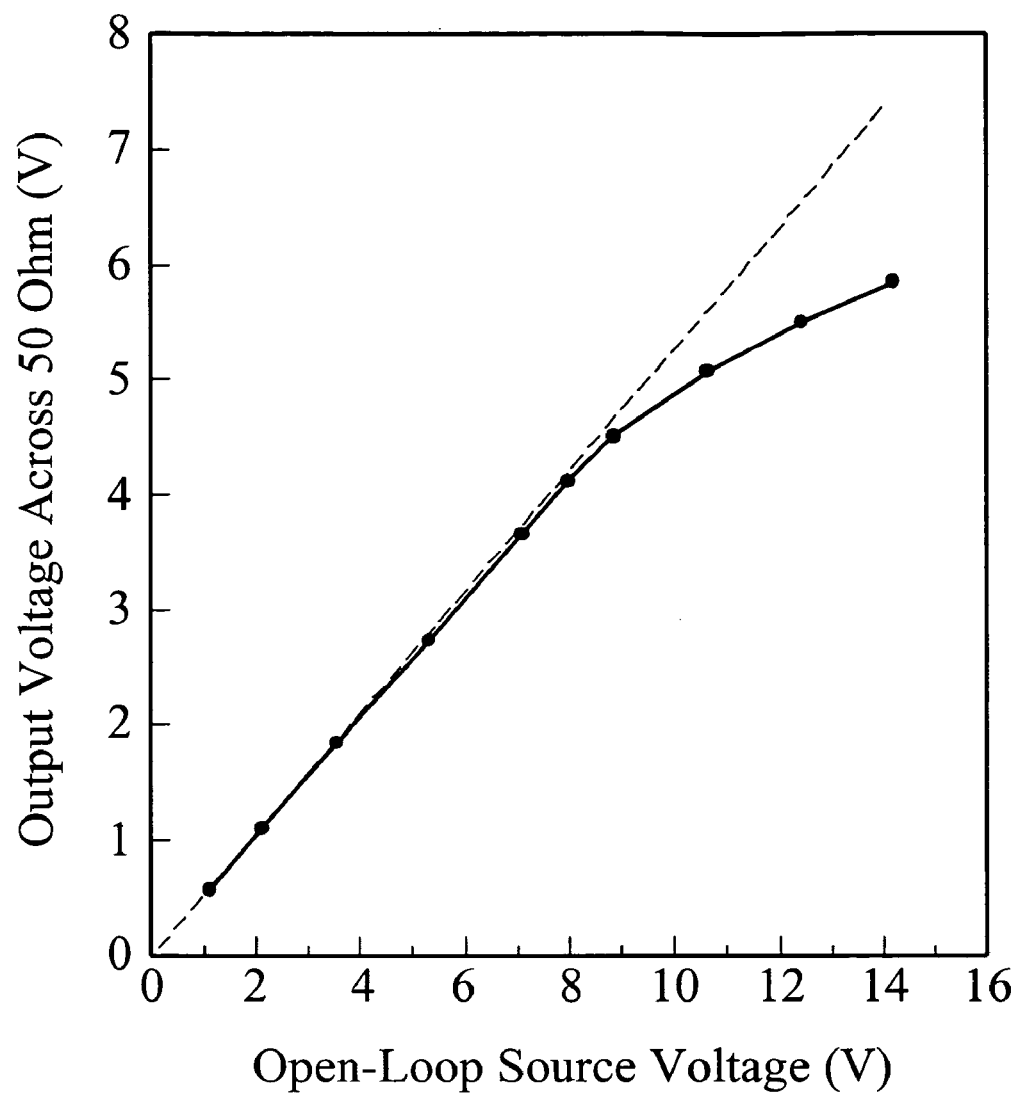
FIG. 18 is a plot depicting the voltage measured across a 50-Ω resistor that is in series with a 14.3-MHz quartz crystal, and the crystal connected with a signal source operated exactly at the crystal's series resonance frequency.

FIG. 18 is a plot depicting the voltage measured across a 50-Ω resistor that is in series with a 14.3-MHz quartz crystal, and the crystal connected with a signal source operated exactly at the crystal's series resonance frequency. Due to the fact that the driving frequency is equal to the series resonance frequency, the crystal can be represented as an ohmic resistor. The plot in FIG. 18 shows that at higher driving voltage the current through the 50-Ω detector input resistor, and therefore the voltage across this resistor, is not following the increasing driving voltage. It should be mentioned that in FIG. 18 the driving voltage is represented as the so-called open-loop source voltage, which is obtained when no electric load is connected to the signal source.

Figure 19:
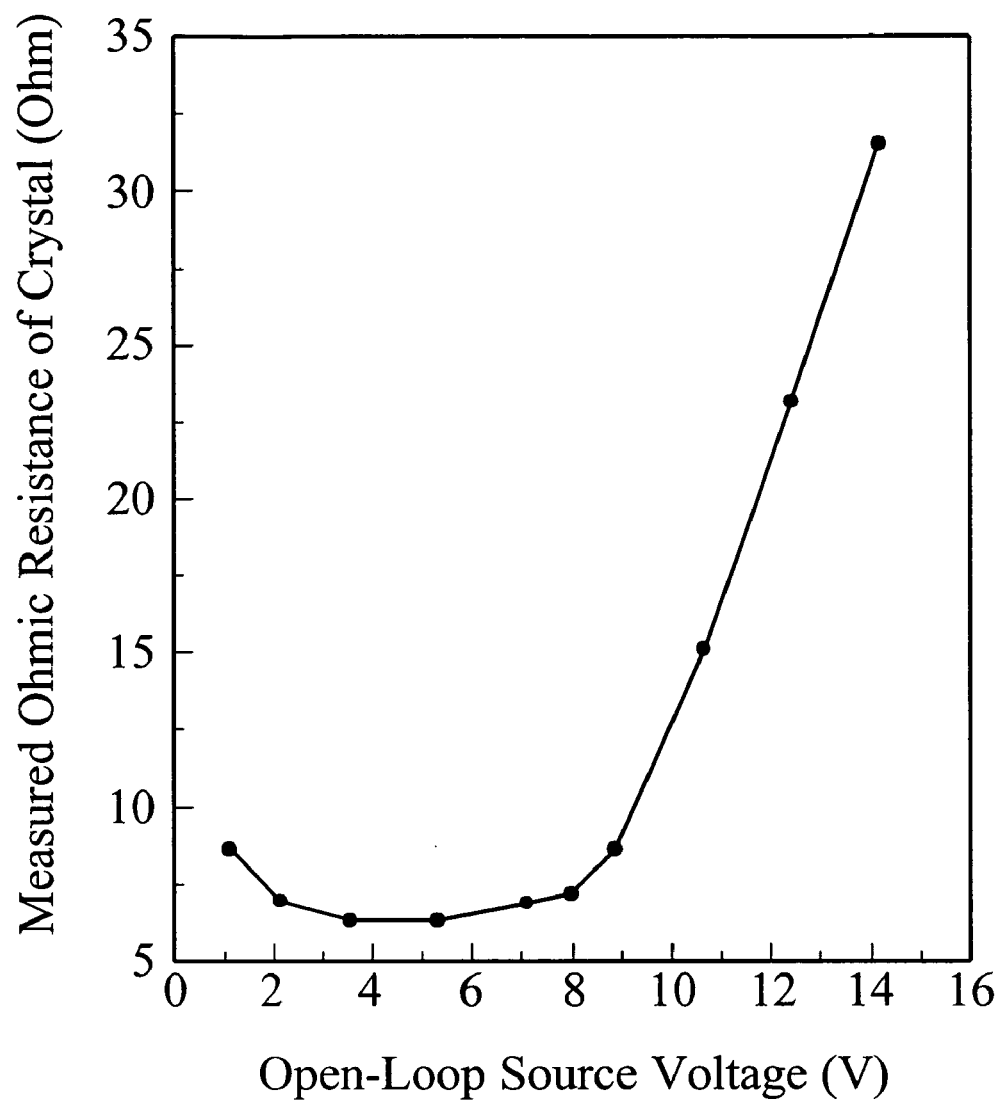
FIG. 19 shows calculated crystal resistance values.

The non-linear behavior of the output voltage in FIG. 18 has to be interpreted as the consequence of a voltage-dependent ohmic crystal resistance. FIG. 19 shows the calculated crystal resistance values, based on the data from FIG. 18. As can be seen, the resistance increases with increasing open-loop source voltage from values around 7Ω at low voltage to values over 30Ω at 14 V, in reasonable agreement with our estimates based on the spectral broadening at increased driving voltage. The voltage-dependent increase in the crystal's ohmic resistance is likely to be caused by an increase in the crystal's temperature. Consequently, the change in the crystal's ohmic resistance occurs at a relatively slow speed.

At a first glance, the slight increase in the width of the resonance spectrum as well as the increase in the crystals' ohmic resistance may appear unimportant. However, depending on the frequency at which the crystal is being operated, changes in the crystal's "effective attenuation" and in its phase shift will occur with increasing driving voltage. This would bring the "balanced comparator circuitry" out of balance, i.e. a non-zero signal would be detected at the input of the RF voltmeter. However, in an apparatus according to an embodiment of the present invention, such as the one illustrated in FIG. 3, computer (10) is keeping the circuitry in balance at all times by adjusting the phase shift and the attenuation within the second channel accordingly. Therefore, the slowly changing voltage-dependent ohmic impedance of the crystal does not cause any concern regarding the feasibility of an acoustic detector according to an embodiment of the present invention.

Experimentation has also revealed that, surprisingly, an acoustic detector according to an embodiment of the present invention can be operated successfully using crystal driving frequencies that fall into a certain range within the crystal's resonance spectrum extending from below the crystal's fundamental series resonance frequency to frequencies above that frequency, whereby the width of said range depends on the degree of liquid loading.

Figure 20:
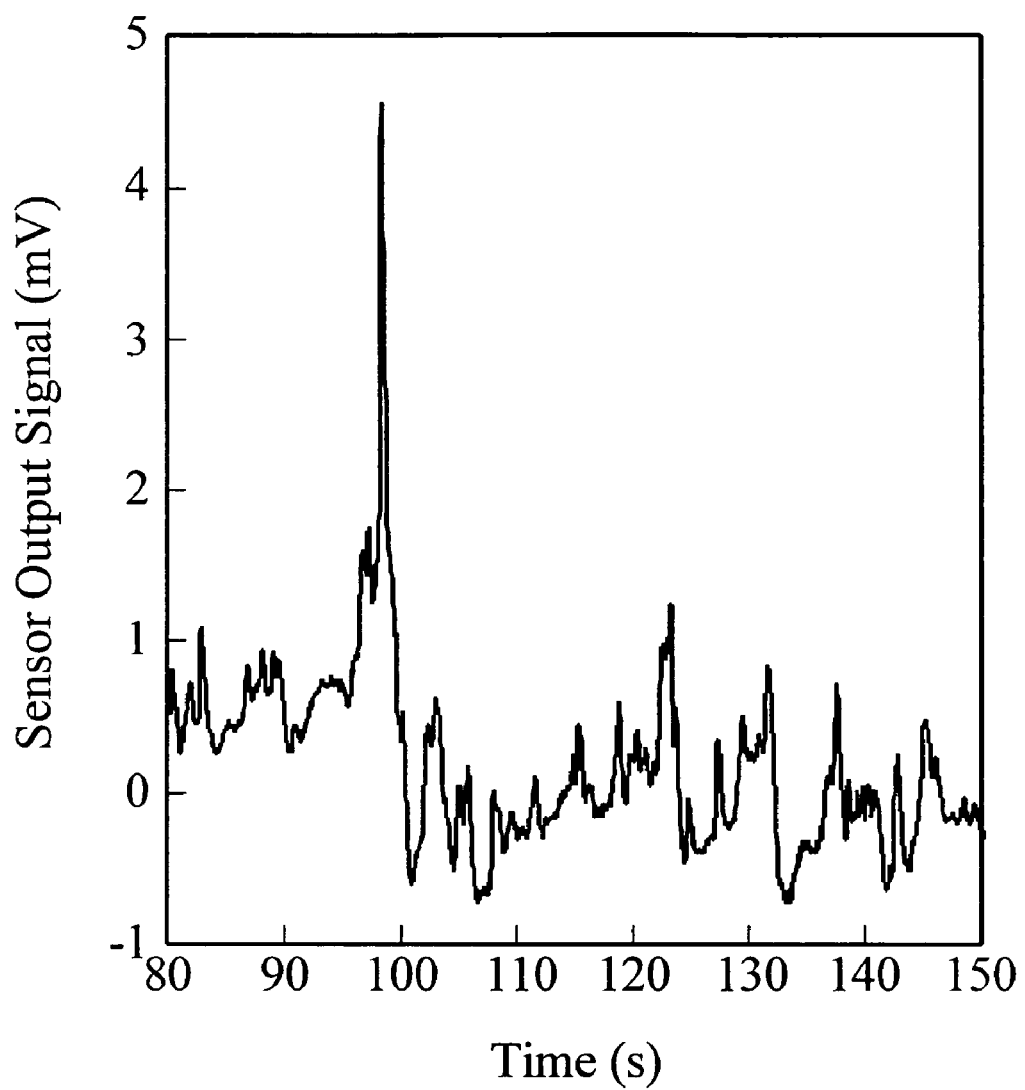
FIG. 20 shows a spike signal recorded near the driving frequency of a 14.3-MHz quartz crystal due to an acoustic shock wave triggered by a micro event.

For purpose of illustration, FIG. 20 shows a spike signal recorded with an apparatus according to an embodiment of the present invention near the driving frequency of a 14.3-MHz quartz crystal due to an acoustic shock wave triggered by a micro event, in this case the "death" of a 100-nL droplet of water. In the experiment illustrated in FIG. 20, the piezo-electric crystal had been exposed to the open air. In other words, no acoustic shielding was used. It has been found, however, that acoustic shielding greatly reduces the noise amplitude of the detected signal. With acoustic shielding, typical peak-to-peak noise signals of approximately 50 µV at 10 V driving voltage and 10 ms detection time constant have been observed. For a detection time constant of 10 ms, transient signals >50 µV can be detected. Depending on the detection time constant used, this threshold level will increase or decrease.

Figure 21:
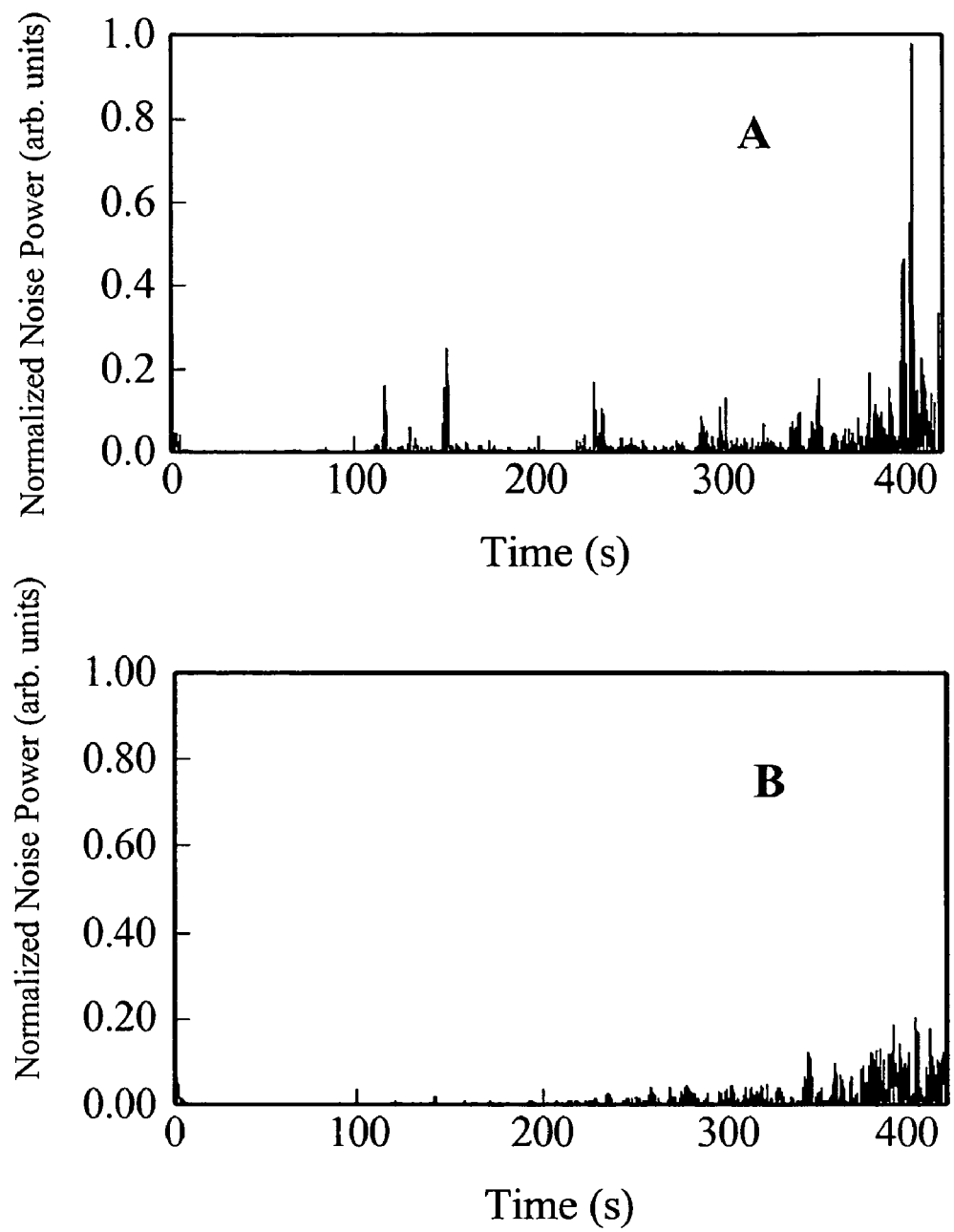
FIG. 21 illustrates experimental data in the form of acoustic REVS spectra recorded near the driving frequency of a 14.3-MHz quartz crystal with (A) plastic PMMA beads attached to the quartz crystal; and (B) with no beads attached.

FIG. 21 illustrates experimental data in the form of acoustic REVS spectra recorded near the driving frequency of a 14.3-MHz quartz crystal with plastic PMMA beads attached to the quartz crystal (A); and with no beads attached (B).

It should be noted that using a sinusoidal driving signal for the piezo-electric crystal and as the second input for the balanced comparator circuitry in an acoustic detector according to an embodiment of the present invention represents a preferred option. However, an acoustic detector according to an embodiment of the present invention could also be operated using other than sinusoidal driving signals. It would be possible, e.g., utilizing a periodic square-wave voltage as the driving signal. Such signal comprises the fundamental frequency and higher harmonics. Even if driven by a square-wave voltage, the crystal would dominantly vibrate in a more sinusoidal fashion. The crystal would act as a frequency filter. Many computer-controlled phase shifters also have a limited frequency range, and would, therefore, also act as a frequency filter. Moreover, if a narrow-band RF voltmeter or even a synchronous detector are used, an additional frequency filtering would take place. Using a square-wave driving signal, combined with a broad-band attenuator, a broad-band phase shifter, and a lock-in amplifier that has "harmonics capability", would allow to operate an acoustic detector according to an embodiment of the present invention at harmonics of the crystal, if desired. Such measure would still be within the spirit of the present invention.

It should also be noted that it would still be within the spirit of the present invention to use, instead of a simple piezo-electric crystal, various surface acoustic wave ("SAW") devices that have at least one surface area designed so that particles in the liquid would bind to the at least one surface area. SAW devices are piezo-electric crystals that are excited by means of lithographically patterned interdigital electrodes. It would also still be within the spirit of the present invention to use acoustic micro-electro-mechanical systems ("MEMS") devices instead of a simple piezo-electric crystal.

While the invention herein disclosed has been described by means of specific embodiments and applications thereof, numerous modifications and variations can be made thereto by those skilled in the art without departing from the scope of the invention as set forth in the claims.

What is claimed is:

1. A detector for use in detecting the presence of particles in a liquid sample comprising:
   a signal generator adapted to provide a driving signal to a transient signal isolation circuit,
   said transient signal isolation circuit comprising a resonant piezo-electric body, an attenuator and phase shifter circuit, a first signal splitting device for directing said transient signal from said signal generator to said resonant piezo-electric body and to said attenuator and phase shifter circuit, and a comparator adapted to receive a first input signal from said resonant piezo-electric body and a second input signal from said attenuator and phase shifter circuit, wherein said comparator generates an output signal based on said first and second input signals, and wherein said resonant piezo-electric body is in contact with said liquid sample;

a transient signal detector adapted to receive said output signal of said comparator and to provide a transient detection signal based on said output of said comparator.

2. A detector as in claim 1, wherein said resonant piezo-electric body and said attenuator and phase shifter circuit are connected in parallel.

3. A detector as in claim 1, wherein said attenuation and phase shifter circuit is adapted to be controlled by a computer.

4. A detector as in claim 1, wherein said signal generator is adapted to be controlled by a computer, and wherein said transient signal detector provides, said transient detection signal to said computer.

5. A detector as in claim 1, wherein said signal generator is adapted to generate signals selected from the group consisting of RF, sinusoidal and non-sinusoidal.

6. A detector as in claim 1, wherein said comparator comprises a transformer.

7. A detector as in claim 1, wherein said comparator comprises a first resistor and a second resistor connected in series between said resonant piezo-electric body and said attenuation and phase shifter circuit.

8. A detector as in claim 7, wherein said input of said comparator is connected to a node between said first and second resistors.

9. A detector as in claim 7, wherein said first and second resistor have substantially equivalent resistance.

10. A detector as in claim 9, wherein said resistance is between 10Ω and 1000Ω.

11. A detector as in claim 9, wherein said resistance is between 100Ω and 10 kΩ.

12. A detector as in claim 1, wherein said comparator comprises a differential amplifier having a first input connected to said resonant piezo-electric body and a second input connected to said attenuation and phase shifter circuit.

13. A detector as in claim 1, wherein said resonant piezo-electric body comprises a resonant crystal selected from the group consisting of a piezo-electric crystal and a surface acoustic wave device.

14. A detector as in claim 4, wherein said transient signal detector is adapted to receive said transient detection signal and to provide said transient detection signal to said computer if said transient detection signal exceeds a threshold.

15. A detector as in claim 4, wherein said transient signal detector is implemented as software running on said computer.

16. A detector as in claim 1, wherein said transient signal detector threshold is adjustable.

17. A detector as in claim 1, wherein said transient signal detector is adapted to generate a transient detection signal that is proportional to said output of said comparator.

18. A detector as in claim 1, wherein said transient signal detector comprises a lock-in amplifier with harmonics capability.

19. A detector as in claim 1, wherein said transient signal detector generates output in digital formal.

20. A detector as in claim 1, wherein said transient signal detector generates output in analog format.

21. A detector as in claim 1, wherein said transient signal detector is a synchronous detector.

22. A detector as in claim 21, wherein said synchronous detector is a lock-in amplifier.

23. A detector as in claim 1, wherein said piezo-electric body comprises at least one surface capable of binding to particles in a liquid sample.

24. A detector as in claim 23, wherein said particles are selected from the group consisting of bacteria and viruses.

25. A detector as in claim 23, wherein said at least one surface comprises antibodies.

26. A detector as in claim 23, wherein said particles comprise particles capable of causing disease in humans.

* * * * *